US008813986B2

(12) United States Patent  
Liscio et al.

(10) Patent No.: US 8,813,986 B2
(45) Date of Patent: Aug. 26, 2014

(54) TOUCHLESS AUTO-DROP SHARPS CONTAINER

(75) Inventors: Michael Liscio, Bellingham, MA (US); Donna Moats, Taunton, MA (US); Mark Brian Finnestad, Franklin, MA (US); Anthony Trupiano, Lakeville, MA (US); Charyn Miller, North Attleboro, MA (US); Derek Ottaviano, Randolph, MA (US)

(73) Assignee: Covidien LP, Mansfield, MA (US)

( * ) Notice: Subject to any disclaimer, the term of this patent is extended or adjusted under 35 U.S.C. 154(b) by 1201 days.

(21) Appl. No.: 12/677,004

(22) PCT Filed: Sep. 6, 2007

(86) PCT No.: PCT/US2007/019442  
§ 371 (c)(1),  
(2), (4) Date: Dec. 7, 2010

(87) PCT Pub. No.: WO2009/031996  
PCT Pub. Date: Mar. 12, 2009

(65) Prior Publication Data  
US 2011/0073598 A1    Mar. 31, 2011

(51) Int. Cl.  
*B65D 83/18* (2006.01)

(52) U.S. Cl.  
USPC .............................. 220/211; 206/366; 206/370

(58) Field of Classification Search  
USPC ........... 318/280, 284, 480; 220/211; 206/365, 206/366, 370  
See application file for complete search history.

(56) References Cited

U.S. PATENT DOCUMENTS

| 3,891,115 A * | 6/1975 | Ono ............................. 220/260 |
| 5,868,709 A | 2/1999 | Champion et al. |
| 6,759,959 B2 | 7/2004 | Wildman |
| 6,859,005 B2 * | 2/2005 | Boliver ........................ 318/480 |
| 6,965,310 B1 | 11/2005 | Hoben et al. |
| 7,275,645 B2 | 10/2007 | Mallett et al. |
| 7,296,688 B2 | 11/2007 | Mallett et al. |
| 7,303,081 B2 | 12/2007 | Mallett et al. |
| 7,303,082 B2 | 12/2007 | Mallett et al. |
| 7,311,207 B2 | 12/2007 | Mallett et al. |
| 7,318,529 B2 | 1/2008 | Mallett et al. |
| 7,341,147 B2 | 3/2008 | Mallett et al. |
| 7,383,195 B2 | 6/2008 | Mallett et al. |
| 7,533,028 B2 | 5/2009 | Mallett et al. |
| 7,533,029 B2 | 5/2009 | Mallett et al. |
| 7,621,898 B2 | 11/2009 | Lalomia et al. |
| 7,660,724 B2 | 2/2010 | Mallett et al. |
| 7,664,656 B2 | 2/2010 | Mallett et al. |

(Continued)

FOREIGN PATENT DOCUMENTS

WO    WO 2009/031996    3/2009

*Primary Examiner* — David Fidei  
(74) *Attorney, Agent, or Firm* — Lisa E. Winsor, Esq.

(57) ABSTRACT

A closure for a waste receptacle is provided. The closure comprises a moveable component mounted to the closure for movement between a closed position, wherein the moveable component prohibits waste from entering the waste receptacle and an open position wherein the moveable component facilitates the entry of waste into the waste receptacle. A motor is coupled to the moveable component and configured to move the moveable component between the open position and the closed position. A sensor is adapted to transmit a signal when waste is proximal or contacting the closure, wherein the sensor communicates with the motor to move the moveable component between the open position and the closed position to deposit the waste into the waste receptacle.

9 Claims, 8 Drawing Sheets

(56) References Cited

U.S. PATENT DOCUMENTS

| | | | |
|---|---|---|---|
| 7,898,201 B2* | 3/2011 | Fisher et al. | 318/466 |
| 2005/0119909 A1 | 6/2005 | Mallett et al. | |
| 2005/0119915 A1 | 6/2005 | Mallett et al. | |
| 2005/0119916 A1 | 6/2005 | Mallett et al. | |
| 2005/0269227 A1* | 12/2005 | Erickson et al. | 206/366 |
| 2006/0200365 A1 | 9/2006 | Mallett et al. | |
| 2006/0212306 A1 | 9/2006 | Mallett et al. | |
| 2006/0212307 A1 | 9/2006 | Mallett et al. | |
| 2006/0218002 A1 | 9/2006 | Mallett et al. | |
| 2006/0253297 A1 | 11/2006 | Mallett et al. | |
| 2006/0265241 A1 | 11/2006 | Mallett et al. | |
| 2007/0175182 A1 | 8/2007 | Stravitz et al. | |
| 2007/0278140 A1 | 12/2007 | Mallett et al. | |
| 2008/0015898 A1 | 1/2008 | Mallett et al. | |
| 2008/0197059 A1 | 8/2008 | Mallett et al. | |
| 2009/0314692 A1 | 12/2009 | Bennett et al. | |

\* cited by examiner

TOUCHLESS AUTO-DROP SHARPS CONTAINER

FIELD OF THE INVENTION

The present invention relates to a medical waste disposal container and more particularly to an automated medical waste disposal container requiring minimal user contact.

BACKGROUND OF THE INVENTION

In hospitals, clinics, and similar medical institutions, contamination continues to be of utmost concern. The prevention of the spread of communicable diseases is a major priority; therefore, disposable, single-use, patient care products have become prevalent. Such items are contaminated, once used, and can readily transmit disease. These items include such devices as hypodermic needles, intravenous needles, razors, scalpel blades, or other sharps—all of which are required to be disposed of at their point of usage under current guidelines of the United States Centers for Disease Control.

Various disposal containers for medical wastes have been proposed for the purpose of accepting medical waste, storing medical waste, and preventing an individual from gaining access to contaminated items once the waste has been deposited into the container, and many such disposal containers go far to accomplish this purpose. One such container is illustrated in U.S. Patent Application No. 2003/0213714 to Moats et al., which is incorporated herein by reference in its entirety.

Nevertheless, there continues to be a need to further develop and improve medical waste disposal systems in the interests of safety, hygiene and convenience.

SUMMARY OF THE INVENTION

According to one aspect of the invention, a closure for a waste receptacle is provided. The closure comprises a moveable component mounted to the closure for movement between a closed position, wherein the moveable component prohibits waste from entering the waste receptacle, and an open position wherein the moveable component facilitates the entry of waste into the waste receptacle. A motor is coupled to the moveable component and configured to move the moveable component between the open position and the closed position. A sensor is adapted to transmit a signal when waste is proximal or contacting the closure. The sensor communicates with the motor to move the moveable component between the open position and the closed position to deposit the waste into the waste receptacle.

According to another aspect of the invention, a foam source is associated with the receptacle. A sensor is adapted to transmit a signal when waste reaches a predetermined level within the receptacle, wherein in response to the signal transmitted by the sensor, a quantity of foam from the foam source is distributed into the receptacle.

According to still another aspect of the invention, a stapling means is coupled to the medical waste receptacle for stapling a guide wire. A slot is disposed on the receptacle for receiving stapled guide wires.

According to still another aspect of the invention, a method of operating an automated medical waste receptacle is provided. The method comprises the step of sensing medical waste contacting or proximal to a moveable component of the receptacle. The method further comprises the step of signaling the moveable component of the receptacle to move from a closed position to an open position to permit the passage of the medical waste into the receptacle.

DETAILED DESCRIPTION OF THE INVENTION

Figure 1:
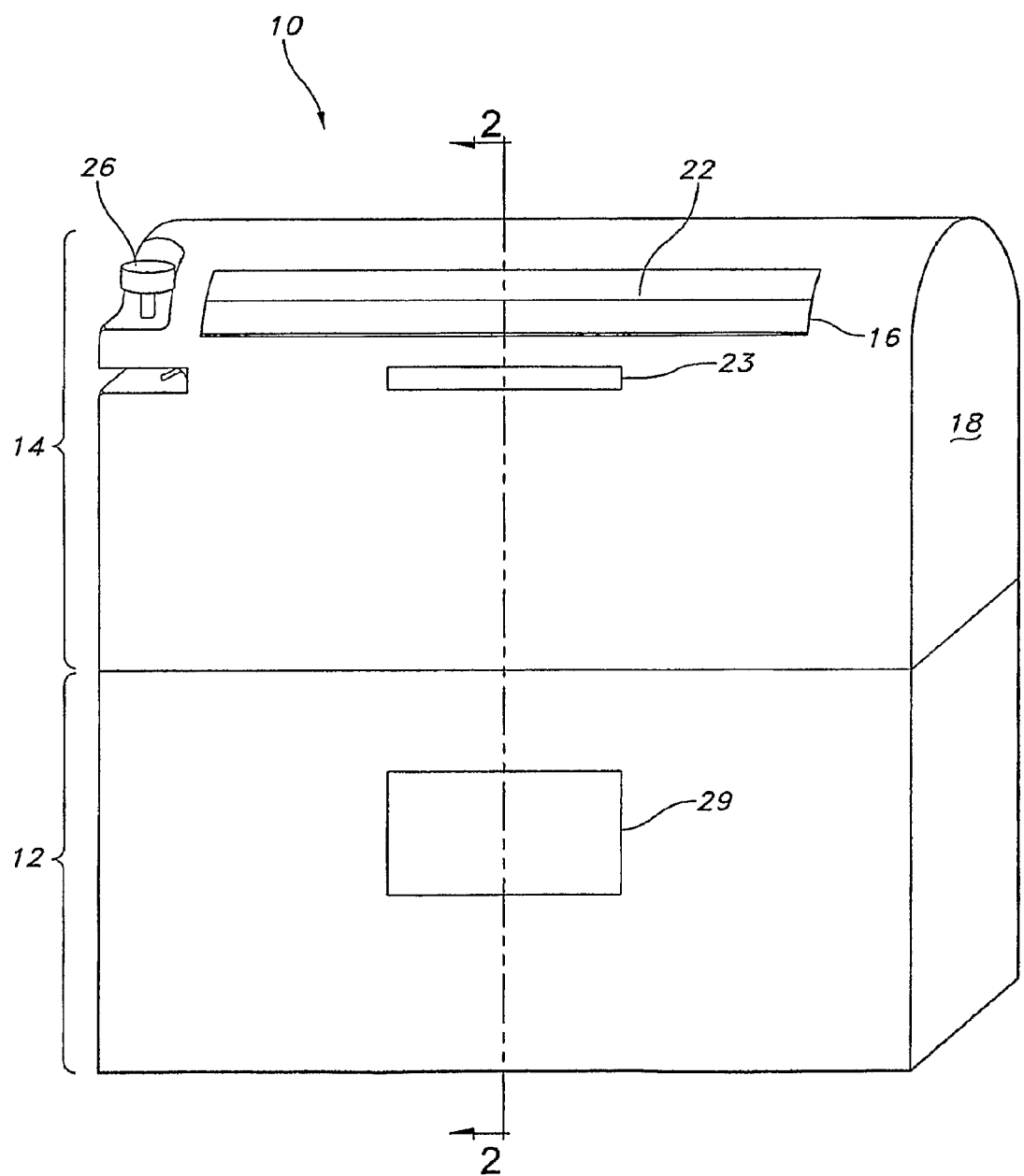
FIG. 1 is a perspective view of an exemplary embodiment of a medical waste disposal system.

Preferred features of embodiments of this invention will now be described with reference to the figures. It will be appreciated that the spirit and scope of the invention is not limited to the embodiments selected for illustration. Also, it should be noted that the drawings are not rendered to any particular scale or proportion. It is contemplated that any of the configurations and materials described hereafter can be modified within the scope of this invention.

Generally, medical waste disposal systems include a receptacle for storing medical waste and some form of a closure assembly that permits the introduction of medical waste into the receptacle while limiting access to the interior of the receptacle. In the interests of safety and convenience, the medical waste disposal system shown in FIGS. 1A-4B includes 'Touchless' features that limit physical contact between the operator and the medical waste disposal system.

Referring now to the figures, a medical waste disposal system embodying exemplary aspects of this invention is generally designated by the numeral "10." The medical waste disposal system 10, hereinafter referred to as waste disposal system 10, disposal system 10, or system 10, is configured to receive and store medical waste 25 including sharps, scalpels, gauze, pipettes, or any other disposable medical waste item. Moreover, the disposal system 10 is not limited to medical waste, as it may contain any item, waste or otherwise.

According to one aspect of the invention, a closure 14 for a disposal system 10 is provided. The closure 14 comprises a tumbler 20, or any other type of moveable component, mounted to the closure for movement between a closed position, wherein the tumbler 20 prohibits waste from entering the disposal system, and an open position wherein the tumbler 20 facilitates the entry of waste into the disposal system. A motor 52 is configured to rotate or pivot the tumbler 20 between the open position and the closed position. A sensor 31 is adapted to transmit a signal to the motor 52 when waste is proximal to or contacting the closure. The motor 52 then rotates the tumbler 20 between the open position and the closed position to deposit the waste into the disposal system.

According to another aspect of the invention, a foam source 37 is associated with the disposal system. A fill level sensor 30 is adapted to transmit a signal when waste reaches a predetermined level within the receptacle 12. In response to the signal transmitted by the fill level sensor 30, a quantity of foam from the foam source 37 is distributed into the receptacle.

According to still another aspect of the invention, a stapling means 26 is position on the disposal system 10 for stapling a guide wire. A slot 23 is disposed on a surface of the disposal system for receiving stapled guide wires.

According to still another aspect of the invention, a method of operating an automated medical waste disposal system is provided. The method comprises the step of sensing medical waste contacting or proximal to a tumbler 20 of the disposal system 10. The method further comprises the step of signaling the tumbler 20 to move from a closed position to an open position to facilitate the passage of the medical waste into the disposal system.

An exemplary embodiment of a "touchless" medical waste disposal system is illustrated in FIGS. 1A-4B. Referring specifically to FIG. 1, a perspective view of an exemplary embodiment of the medical waste disposal system 10 is shown. The medical waste disposal system 10 comprises a receptacle 12 for storing waste items and a closure 14 positioned over the receptacle 12. The system 10 may be referred to in the art as a mailbox-style sharps disposal container. The receptacle 12 defines an interior chamber for storing waste items of any size or shape, as the receptacle 12 is not limited to any particular size or shape. An optional transparent window 29 may be disposed on a surface of the receptacle 12 to enable viewing of the items within the receptacle 12, such that a user may visually observe the level of waste within the receptacle 12.

The closure 14 is an assembly including an outer shell, referred to as a hood 18. The hood 18 is a hollow shell defining an aperture 16 through which waste is deposited. The aperture 16 may be sized to accept waste of any size and is not limited to the illustration. A door 22 is positioned with or coupled to the hood 18 (or any other component of closure 14). The door 22 rotates, pivots or translates within the interior of the hood 18 to conceal or expose the aperture 16. Although not shown, the door may be positioned on the exterior of the hood 18. In an open position (as shown in FIG. 1), the door 22 is positioned to expose the aperture 16 thereby permitting the passage of waste therethrough. In a closed position, the door 22 conceals the aperture 16 to prevent the passage of waste through the aperture 16. The closure 18 also includes a guide wire stapler 26 and guide wire slot 23, which will be described in greater detail with reference to FIGS. 4A and 4B.

Although not explicitly shown in the drawing figures, the closure 14 may be releasably or permanently mounted to receptacle 12. For example, the closure 14 may be welded (e.g., ultrasonically, adhesively, thermally, and so forth) and hermetically sealed to receptacle 12 to limit leakage of waste or foam at the interface between closure 14 and receptacle 12. Alternatively, the closure 14 may be releasably mounted to receptacle 12 by tabs, screws, or any other releasable fastening means known in the art, so that closure 14 may be reused after a filled receptacle is replaced with an empty receptacle 12, if so desired. The closure 14 and/or receptacle 12 may include a mounting surface, shoulder or alignment feature (not shown) at the interface of the closure 14 and the receptacle 12 to facilitate releasable or permanent mounting of the closure 14 onto the receptacle 12.

Figure 2A:
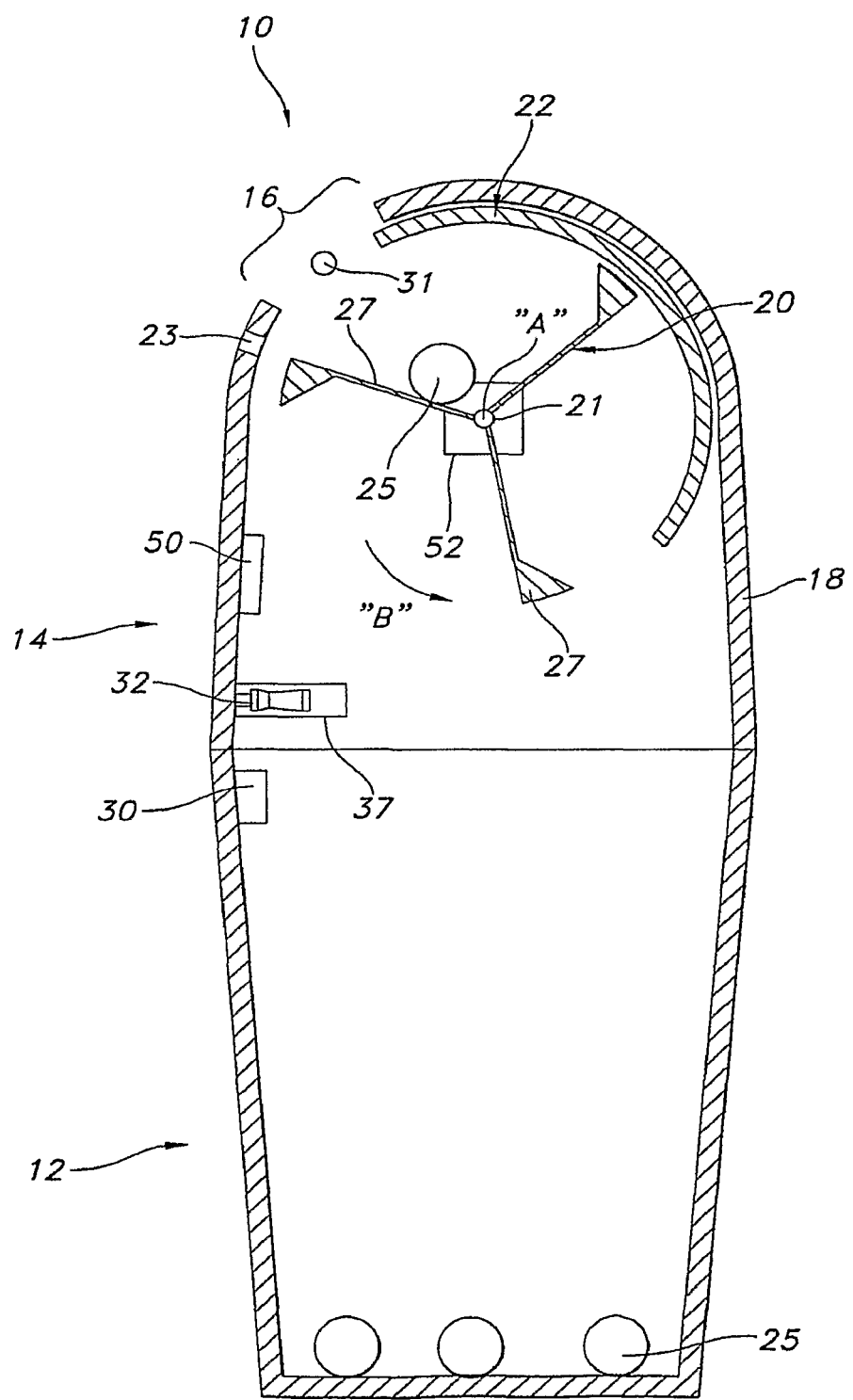
FIG. 2A is a cross-sectional view of the medical waste disposal system of FIG. 1 taken along the lines 2-2, wherein a door of the medical waste disposal system is rotated to an open position.
Figure 2B:
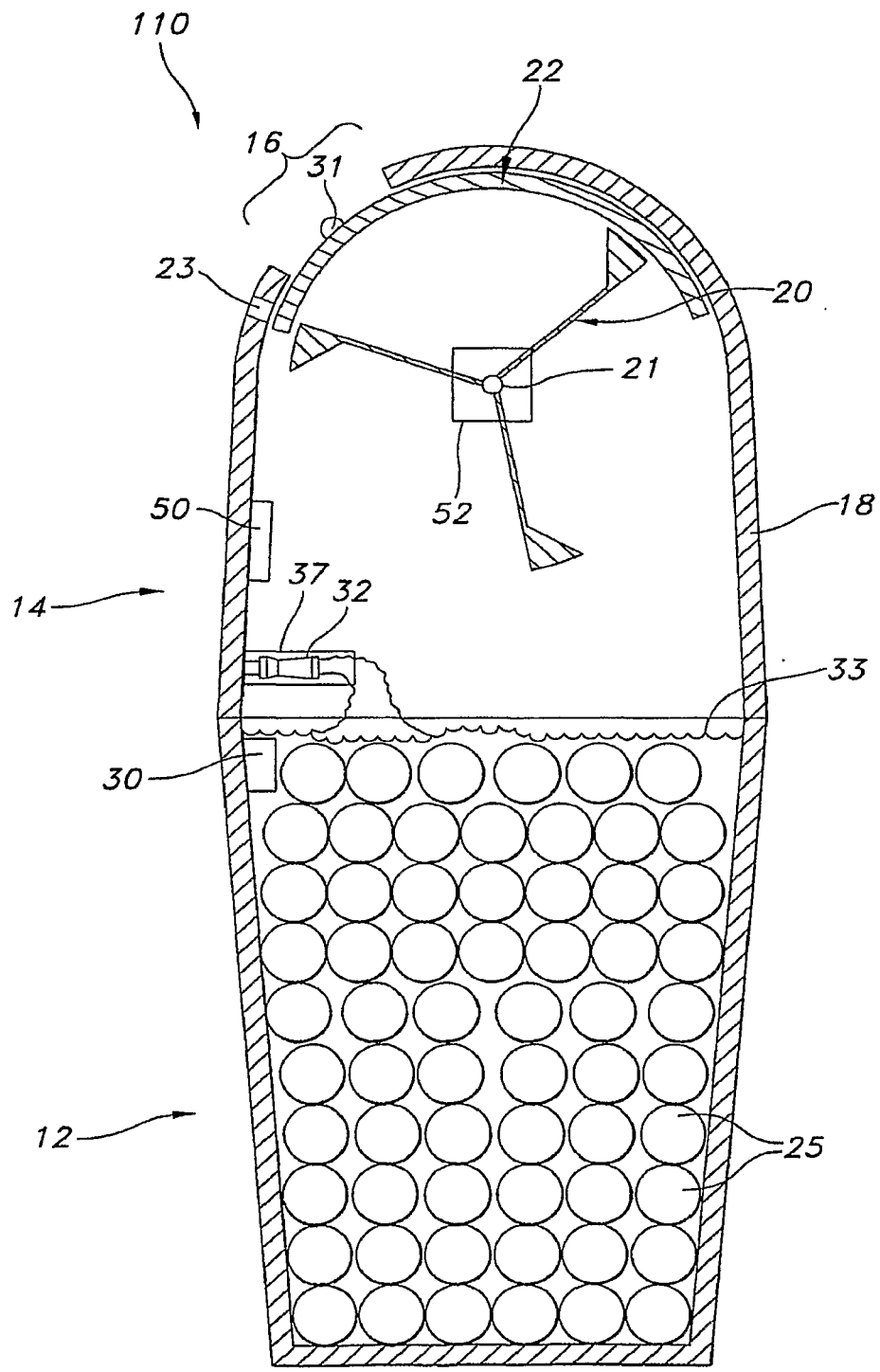
FIG. 2B is a cross-sectional view of the medical waste disposal system of FIG. 1 taken along the lines 2-2, wherein the system is filled with waste encapsulated by foam, and the door of the medical waste disposal system is rotated to a closed position.

Referring now to FIGS. 2A and 2B, a cross-sectional view of the medical waste disposal system 10 of FIG. 1 taken along the lines 2-2 is shown in FIG. 2A, wherein the door 22 of the medical waste disposal system is rotated to an open position to receive medical waste 25. The medical waste disposal system 110 shown in FIG. 2B is identical to the disposal system 10 shown in FIG. 2A, however, the disposal system 110 is filled with medical waste 25 and foam 33, and the door 22 is rotated to a closed position.

As best shown in FIGS. 2A and 2B, a tumbler 20 rotates about axis "A" to discharge waste 25 into the receptacle 12. The tumbler 20 is configured to rotate about axis of revolution "A" in a counter-clockwise direction, for example, as indicated by directional arrow "B." It should be understood that the tumbler 20 may also be configured to rotate in a clockwise direction.

The tumbler 20 includes a rod 21, which defines axis "A", and a plurality of arms 27 (three shown) which extend from the rod 21. The arms 27 of the tumbler 20 create a tortious path to limit or prevent an unauthorized user from reaching through the aperture 16 to retrieve medical waste from within the receptacle 12. The tumbler 20 is not limited to the illustration shown, as other structures known in the art are contemplated. For example, although not shown, in lieu of a tumbler, the closure 14 may include a lid coupled to an interior surface of hood 18 by a living hinge that is pivoted to selectively expose or conceal the aperture 16. Accordingly, the tumbler 20 is also referred to herein as a movable component.

In this exemplary embodiment, tumbler 20 is optionally coupled to a motor 52, as shown in FIGS. 2A and 2B. Although not explicitly shown in FIGS. 2A and 2B, the rod 21 of the tumbler is directly coupled to an output shaft of the motor 52 (see FIG. 3B). The motor 52 is configured to rotate the rod 21 of the tumbler in direction "B" once waste is placed on or near the tumbler, as described in greater detail with reference to FIGS. 3A and 3B. The motor 52 may be configured to rotate the tumbler 20 in either a clockwise or counterclockwise direction, depending upon the user requirements. Upon rotation of the tumbler 20, the medical waste 25 ultimately descends into the receptacle 12. The automated tumbler 20 virtually eliminates any necessity for a user to manually rotate the tumbler 20 by hand. However, it should be understood that the motor 52 is an optional component of the waste disposal system.

In another exemplary embodiment not illustrated herein, the motor 52 is omitted from the closure 14. In that embodiment, the tumbler 20 is biased by gravity to rotate under the weight of medical waste placed thereon without human intervention. In a stationary position, two arms 27 of the tumbler 20 are oriented toward the receptacle 12 under gravity, and the third arm 27 are oriented toward the top surface of hood 18. Once a waste item 25 is deposited through aperture 16, the waste item descends onto one of the arms 27 causing the tumbler 20 to rotate in either a clockwise or counter-clockwise direction. Once the tumbler has rotated sufficiently, the waste item slides along a surface of the arm 27 and descends into the receptacle 12. Although a cost savings may be achieved by omitting the motor 52, it should be understood that in certain circumstances, a medical waste item may not be of sufficient weight to cause the tumbler 20 to rotate without human intervention, thereby necessitating manual rotation of the tumbler 20. Therefore, the motor 52 is a particularly beneficial feature of the waste disposal system 10 in the interest of safety, convenience and hygiene.

The system 10 includes an automated door 22 to selectively permit or prohibit access to the interior of the closure 14. The door 22 is configured to rotate or pivot about axis "A" with respect to the aperture 16 of the hood 18 between an open and a closed position to either expose or conceal the aperture 16, as shown in FIGS. 2A and 2B, respectively. The door 22 is illustrated in an open position (i.e., the aperture 16 is exposed) in FIG. 2A, and the door 22 is illustrated in a closed position (i.e., the aperture 16 is concealed) in FIG. 2B. Although not explicitly shown in FIGS. 2A and 2B, the door 22 may be directly or indirectly coupled to the hood 18, the tumbler 20, the output shaft of the motor 52, the rod 21 of the tumbler 20, and/or any other component of the closure 14.

The door 22 is an optional feature of the medical waste disposal system 10. Depending upon the requirements of the user, the system 10 may only include the tumbler 20 for permitting or prohibiting the passage of waste into the receptacle 12. Moreover, the door 22 may be an automated or manual component depending upon the configuration of the system 10. Although not shown, if the door 22 is manually operable, a door handle may be provided for a user to conveniently rotate the door 22 between the open and closed positions. The handle may be a separate component mounted to the door 22, or integrated with the body of the door 22.

The door 22 is not limited to the illustration shown, as other structures known in the art are contemplated. For example, the door may slide along a slot or groove disposed in the hood 18, or, alternatively, the door may be pivotably coupled to an interior or exterior surface of the hood 18 by a living hinge, or any other style of hinge. The door 22 and the hood 18 may also include a manual or automated locking feature (not shown) such that once the door 22 is rotated to the closed position it can not be reopened without applying significant force.

Figure 3A:
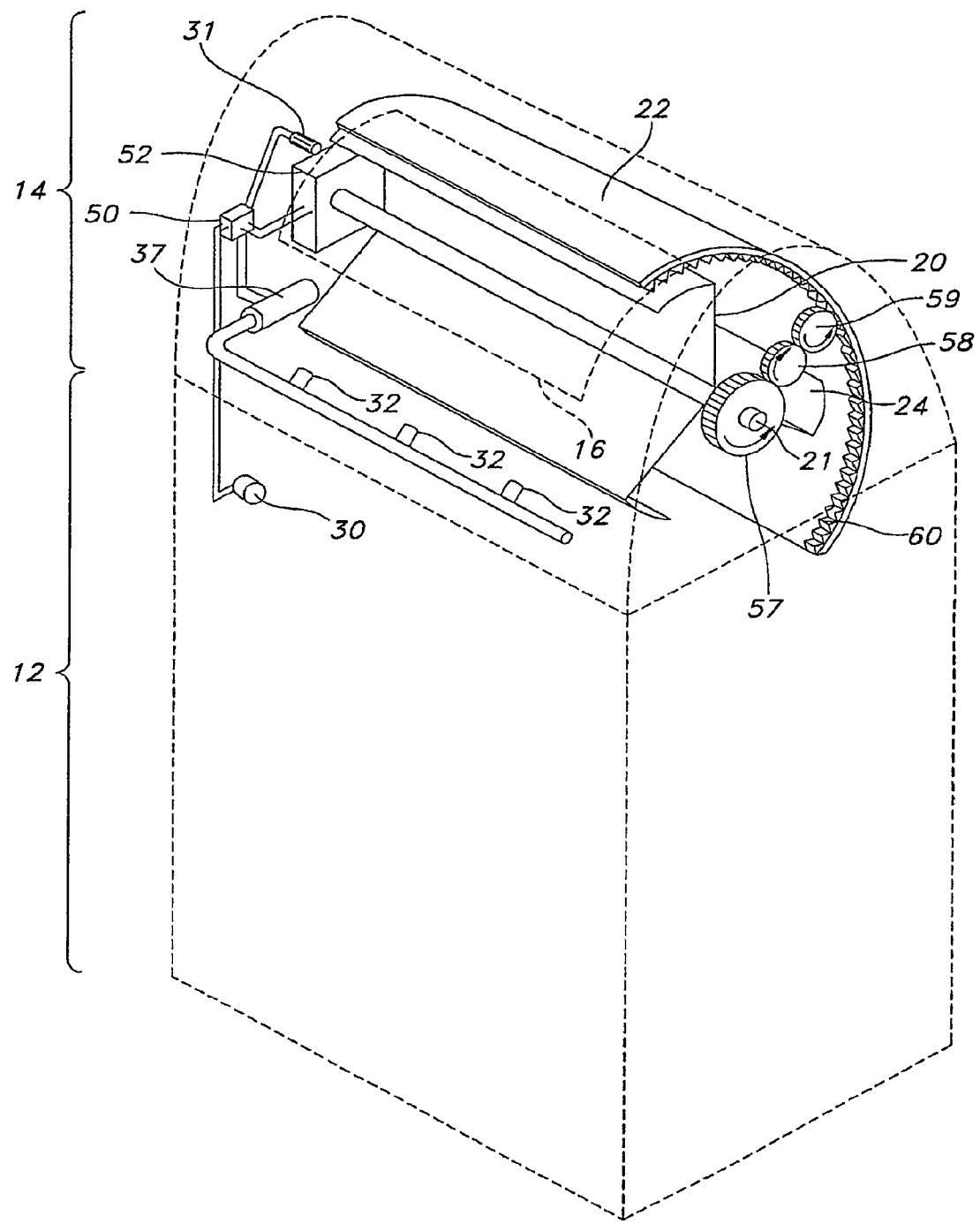
FIG. 3A is a perspective cut-away view of the medical waste disposal system of FIG. 1, illustrating the internal components of the waste disposal system schematically.
Figure 3B:
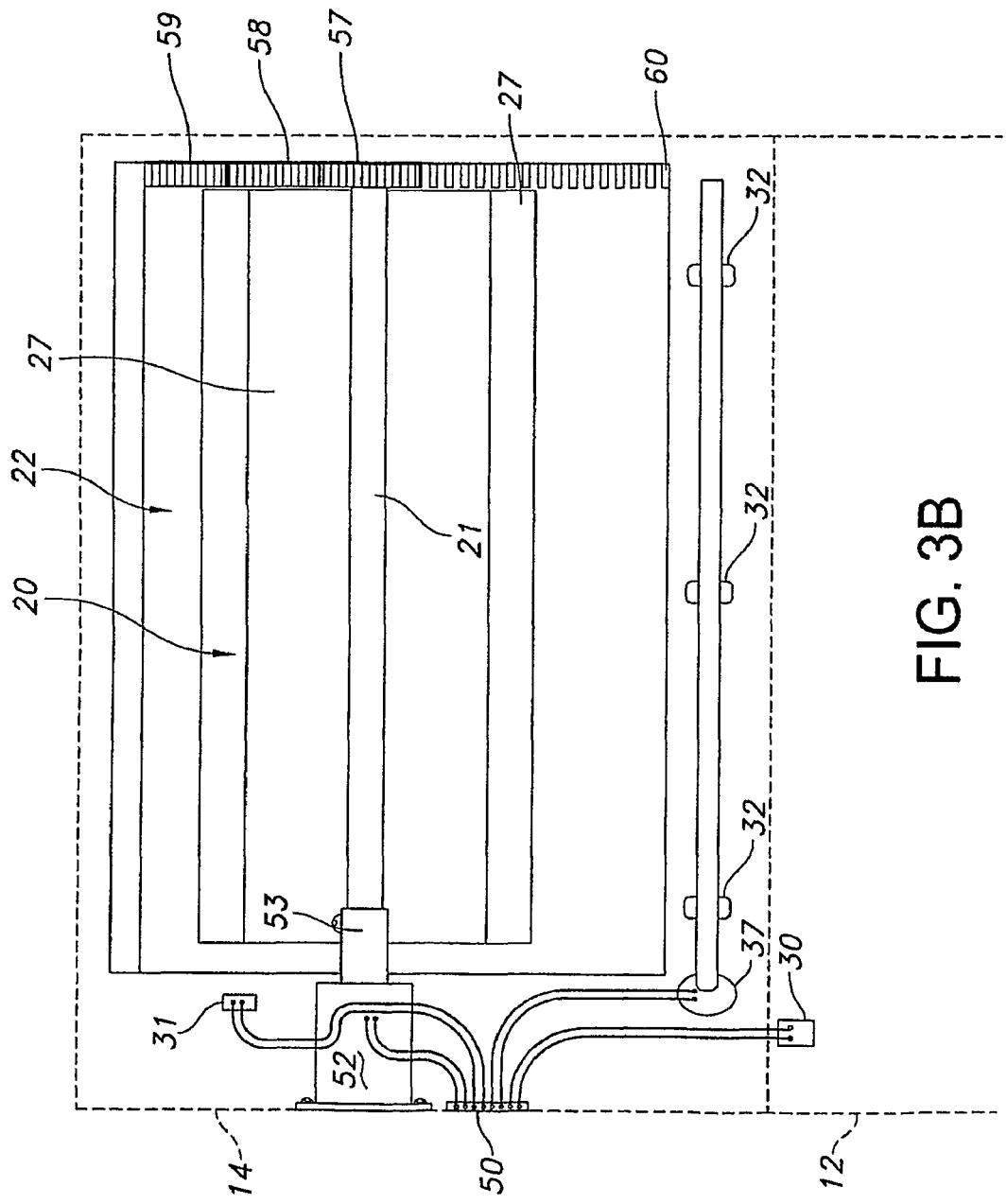
FIG. 3B is a front view of the medical waste disposal system of FIG. 3A, shown schematically.

Referring now to FIGS. 3A and 3B, a perspective view and a front view of the internal components of the disposal system 10 are respectively shown. The tumbler 20 is directly coupled to the motor 52. Specifically, the rod 21 of the tumbler 20 is positioned within the output shaft 53 of the motor 52, and the rod 21 is fixedly mounted to the output shaft 53 by a fastener. The output shaft 53 of the motor 52 transfers rotational motion to the tumbler 20. One skilled in the art will recognize that the tumbler 20 may be mounted to the motor 52 in a variety of different fashions to achieve the same purpose. For example, the motor 52 may be coupled to the tumbler 20 by a gear, belt, linkage or any other apparatus known in the art.

According to the exemplary embodiment, rotational motion of the output shaft 53 of the motor 52 is transferred to the door 22 through a series of gears 57, 58 and 59. More specifically, gear 57 is fixedly mounted to the proximal end of the rod 21 of the tumbler 20, such that gear 57 and rod 21 rotate simultaneously in the same rotational direction. The teeth of gear 57 engage the teeth of the adjacent gear 58, causing the gears 57 and 58 to rotate in opposite rotational directions. The teeth of gear 58 engages the teeth of an adjacent gear 59, causing the gears 58 and 59 to rotate in opposite rotational directions, as indicated by the arrows on the gears. The teeth of gear 59 engage with gear teeth 60 disposed on the proximal end of the door 22, such that the gear 59 and door 22 rotate in the same rotational direction. It should be understood that the door 22 and gear 57 rotate in the same rotational direction. Although not shown, the gears 57 and 58 may be mounted to the hood 18 (or another surface of the closure 14) at a fixed location by a pin, screw, rivet, or any other type of fastener that permits the gears 57 and 58 to freely rotate about their respective axes without translating. One skilled in the art will recognize that the rotational motion of the output shaft 53 of the motor may also be directly or indirectly transferred to the door 22 by a linkage, cam, pulley, or any other mechanical or electrical apparatus to achieve the same purpose. Also, although not shown, the tumbler 20 and the door 22 may be powered by separate motors. As mentioned above, the door 22 may be manually operable (i.e., not coupled to a motor).

Referring still to the exemplary embodiment illustrated in FIGS. 3A and 3B, the system is configured to rotate the tumbler 20 more than 120 degrees so that the waste item may descend into the receptacle 12 under its own weight. Because the door 22 rotates along with the tumbler 20, the system 10 is configured to return the door 22 to the open position (see FIG. 2A) so that the medical waste disposal system 10 may continue to accept more waste.

In this exemplary embodiment, the motor 52 is configured to rotate the tumbler 20 and the door 22 in response to signals generated by a motion sensor 31. The motion sensor 31 is positioned adjacent to the aperture 16 on either the inside or the outside of the closure 14. The motion sensor 31 is configured to sense an approaching waste item or an approaching hand of a user. In response to that motion, the motion sensor 31 transmits a signal to a signal processor/controller 50 until the motion sensor 31 no longer senses the approaching hand or medical waste item (indicating that the user has moved his or her hand away from the aperture 16). The signal processor/controller 50 then transmits a signal to the motor 52 causing the motor 52 to rotate the tumbler 20 in the counter-clockwise direction "B." Rotation of the motor induces rotation of the tumbler 20, and the waste item 25 positioned on an arm 27 of the tumbler 20 ultimately descends into the receptacle 12. The motor 52 rotates the tumbler 20 and the door 22 until the door 22 returns to an open position so that the system 10 is readily available to accept more waste.

Although not shown, in lieu of, or in addition to the motion sensor 31, the system 10 may include a weight sensor associated with the tumbler 20. In such an embodiment, the weight sensor is configured to transmit a signal to the signal processor when a waste item is placed onto the tumbler 20. The weight sensor may be capable of detecting a force of greater than or equal to about 0.01 grams, or, alternatively, the weight sensor may be capable of detecting a force of greater than or equal to about 0.1 grams.

According to the exemplary embodiment illustrated in FIGS. 3A and 3B, the signal processor and the controller are integrated into a single component. However, in another embodiment, the signal processor and the controller may be separate components.

Referring now to FIGS. 2A through 3B, a fill level sensor 30 positioned on or within the receptacle 12 is configured to sense when the level of the medical waste within the receptacle 12 has reached a predetermined level (e.g., ¾ full). At that moment, the fill level sensor 30 is configured to transmit a signal to the signal processor/controller 50. The signal processor/controller 50 subsequently instructs the motor 52 to rotate the door 22 to the closed position (the tumbler 20 rotates as well) shown in FIG. 2B. Alternatively, if the door 22 is not automated, the system 10 could signal the user to move the door 22 to the closed position. The fill level sensor 30 may be positioned on a surface of the receptacle 12, the closure 14 or any appropriate surface of system 10.

The motion sensor 31 and/or the fill level sensor 30 can comprise any device capable of detecting motion and/or changes in the environment around the sensor, such as active or passive sensors. Active sensors are capable of emitting energy and detecting changes in the emitted energy. For example, in one embodiment, a motion sensor can comprise a photoemitter and a photodetector, wherein the photoemitter is capable of emitting ultraviolet light which is reflected by an aptly positioned surface such that the reflected ultraviolet light is sensed by the photodetector. In such active sensors, the emitter and sensor can be configured as one component (e.g., utilizing a reflection of the emitted energy) or as multiple components (e.g., an emitter disposed on a first side of the closure 14 or the receptacle 12 and a detector disposed opposite to the emitter on an opposing side of the closure 14 or the receptacle 12). In alternative embodiment, the active sensors emit other forms of energy, such as visible light, infrared light, sound waves, and so forth. The motion sensor may also comprise passive sensors, such as charge coupled devices capable of detecting infrared energy, hall-effect sensors, radiofrequency sensors, and so forth. In one specific embodiment, an infrared sensor (e.g., commercially available from Panasonic Inc.) can be employed to detect the thermal energy emitted by a user's body as it approaches the aperture 16 when waste is disposed therein.

The motion sensor 31 and/or the fill level sensor 30 may be configured to detect waste that is in close proximity. For example, the sensors may be configured to detect waste that is less than or equal to about 6 inches away from the sensors, or more specifically, less than or equal to about 3 inches away from the sensors, or even more specifically, less than or equal to about 1 inch away from the sensors.

As described previously, the door 22 and the hood 18 may include a manual or automated locking feature to secure the door 22 in the closed position. In another exemplary embodiment not illustrated herein, an electromechanical lock is mounted to the closure 14. Upon receiving a signal from the fill level sensor 30 indicating that the receptacle 12 is sufficiently filled with medical waste, the signal processor/controller SO is configured to activate the electromechanical lock to secure the door 22 and/or the tumbler 20 in a stationary position once the door 22 is rotated to the closed position.

After the waste within the receptacle 12 has reached a predetermined level and the door 22 is locked in the closed position, the signal processor/controller 50 is configured to transmit a signal to a pressurized foam source 37 that is fluidly connected to foam injection ports 32 positioned throughout the closure 14 and/or the receptacle 12. In response to that signal, the pressurized foam source 37 distributes foam to the foam injection ports 32, which are configured to inject foam 33 throughout the receptacle 12, as best shown in FIG. 2B.

The foam 33 is schematically represented by swirl patterns shown in FIG. 2B. The foam injection ports 32 may optionally inject enough foam 33 to fill the entire waste disposal system 10 or just the receptacle 12, as shown in FIG. 2B. The foam eventually solidifies and encapsulates the waste contents within system 10. The contents of the foam 33 may include one or more hardening, anti-microbial, and/or disinfection agents to encapsulate and neutralize the soiled contents of the system 10. The foam 33 may optionally comprise one or more polymers and a curing agent. The curing agents may include moisture, air, crosslinking agents, chemical crosslinking or RTV, for example. Exemplary polymers may be polyurethanes, ureas, acrylics, epoxies, or polystyrene, for example.

The process of foam encapsulation is particularly beneficial from a safety perspective by reducing exposure to infectious waste. More particularly, if the system 10 is unintentionally opened, or otherwise damaged in use or upon shipment, escapement of the foam encapsulated waste contents from the system 10 is substantially reduced.

After the system 10 is filled with medical waste and foam, the entire system 10 may be disposed and replaced with a new waste disposal system 10. However, in another exemplary embodiment not illustrated herein, the sensors 30 and 31, motor 52, signal processor/controller 50, pressurized foam source 37 and/or foam injectors 32 may be incorporated into a unit separable from the receptacle 12 and closure 14. In this exemplary configuration of system 10, many of the electro-mechanical components can be recovered and reused with a replacement waste disposal system 10. It is contemplated that this configuration of system 10 could represent a significant cost savings to the end user.

Figure 4A:
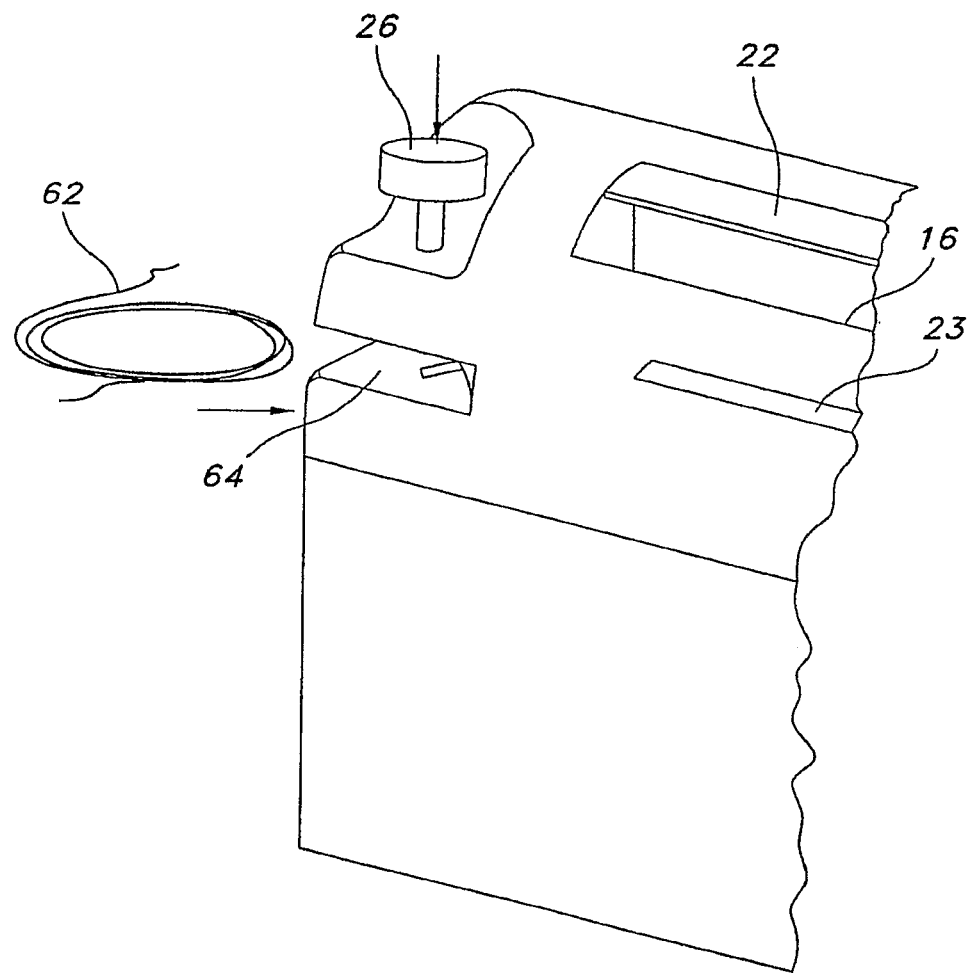
FIG. 4A is a detailed view of a stapler of the medical waste disposal system of FIG. 1, and a coiled guide wire in preparation for stapling.
Figure 4B:
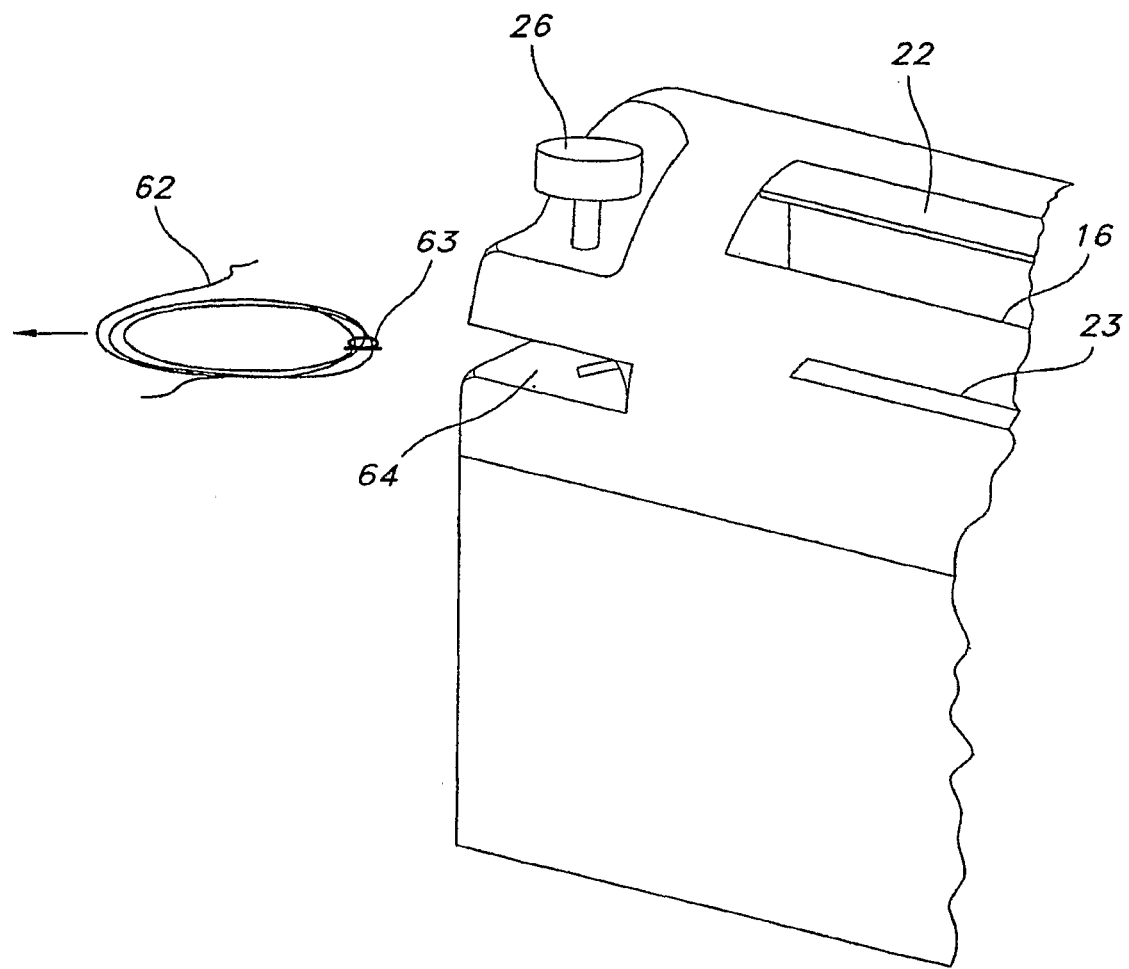
FIG. 4B is a detailed view of the stapler of FIG. 4A and a stapled coiled guide wire.

Referring now to FIGS. 4A and 4B, the disposal system 10 may optionally include a guide wire stapler 26 and a guide wire disposal slot 23 disposed on the closure 14. As background, in a variety of medical procedures, a flexible guide wire 62 is fed through a blood vessel, artery or any other lumen of the human body. For example, in an angioplasty procedure, a guide wire 62 is fed through a blood vessel of a patient to clear a blockage in the vessel. After the guide wire 62 is removed from the body of the patient, it is commonly coiled into a manageable cylindrical shape, as shown in FIG. 4A. There is a need to provide a simple and sanitary approach to dispose of soiled guide wires. To that end, disposal system 10 includes a guide wire stapler 26 and a guide wire disposal slot 23.

In practice, the coiled guide wire 62 is inserted into a recess 64 formed on the top end of the closure 14, as indicated by the horizontal arrow in FIG. 4A. The guide wire stapler 26 is then manually depressed, as indicated by the vertical arrow in FIG. 4A, to staple the convolutions of the coiled guide wire 62 together with a staple 63. The guide wire 62 is thereby retained in a manageable shape for disposal purposes. The stapled guide wire 62 is then removed from the recess 64, as indicated by the horizontal arrow shown in FIG. 4B. Thereafter, the stapled guide wire 62 may be disposed of through the guide wire disposal slot 23 positioned beneath the aperture 16. The guide wire stapler 26 may be an automated or manual-style stapler, as shown. The guide wire stapler 26 and guide wire disposal slot 23 are optional features of the disposal system 10.

Figure 5:
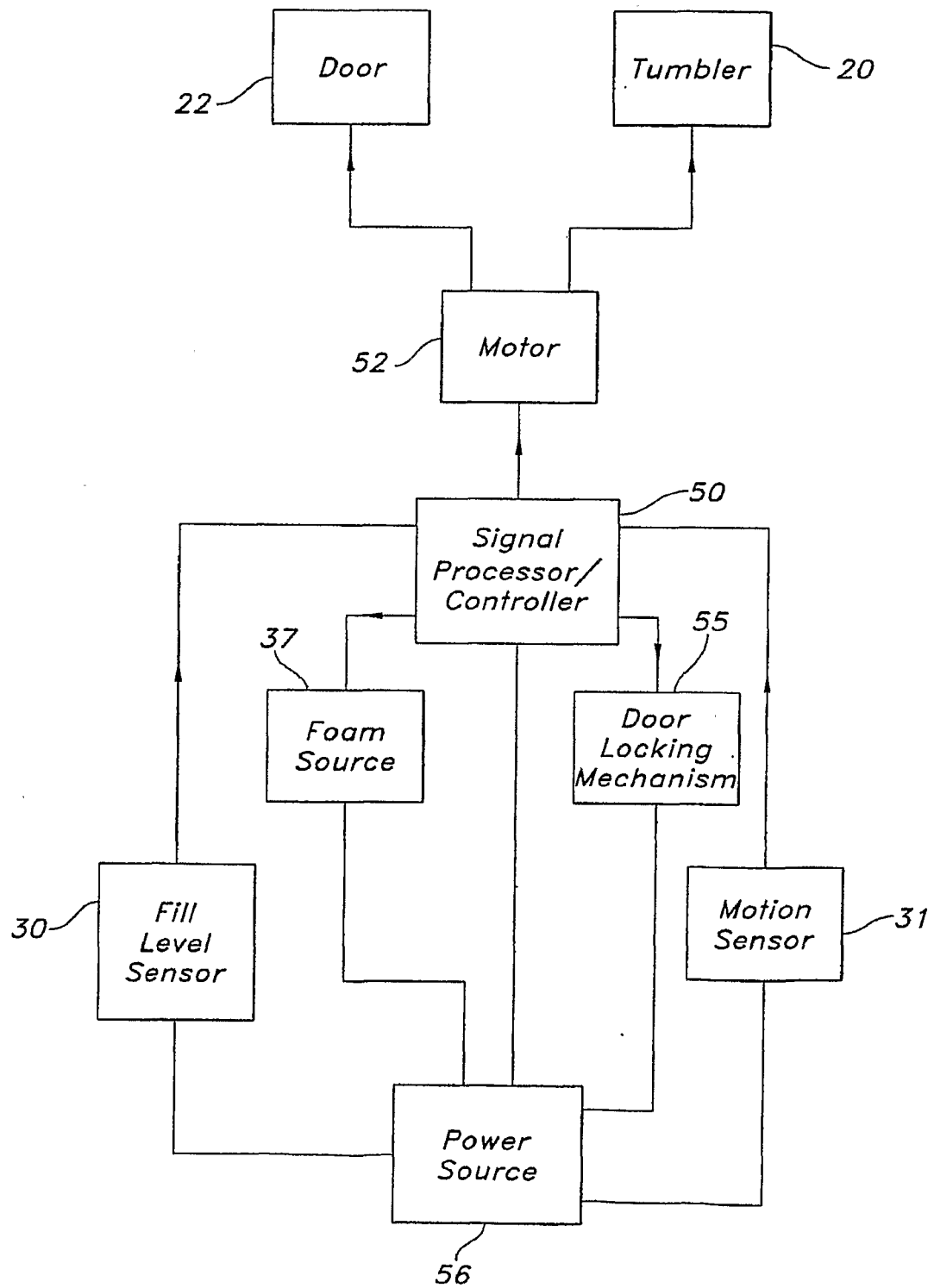
FIG. 5 is a schematic block diagram of the electromechanical components of the medical waste disposal system of FIG. 1.

Referring now to FIG. 5, a schematic block diagram of the electrical and mechanical components of system 10 are illustrated. The motor 52, the motion sensor 31, the fill level sensor 30, the door locking mechanism 55 (not shown in other Figures), and the signal processor/controller 50 are connected to a power source 56. The motion sensor 31 and fill level sensor 30 are configured to transmit an electrical signal to the signal processor/controller 50. The signal processor/controller 50 is configured to transmit a signal to the motor 52, the foam source 37 and the door locking mechanism 55. The tumbler 20 and the door 22 are mechanically coupled to the door motor 52, as shown schematically. In response to a signal from the signal processor/controller 50, the motor 52 is configured to rotate the tumbler 20 and the door 22.

Referring now to the prospective materials of the system 10, the receptacle 12, closure 14, tumbler 20, and door 22 may be formed from any appropriate material, metallic or a polymeric material. The specific polymers employed for the receptacle 12, closure 14, tumbler 20, and door 22 may provide puncture resistance to withstand puncture from needles or scalpels descending into the receptacle. Additionally, the material of the receptacle 12 may be impact resistant, fire-retardant, waterproof to prevent leakage of the waste from the receptacle, and/or transparent to enable viewing of the items within the receptacle 12.

Exemplary polymeric materials include polyalkylenes (e.g., polyethylene, polypropylene, polyalkylene terephthalate (such as polyethylene terephthalate, polybutylene terephthalate)), polycarbonate, acrylic, styrenes (e.g., impact-modified polystyrene, acrylonitrile-butadiene-styrene, styreneacrylonitrile), poly(meth)acrylate (e.g., polybutyl acrylate, polymethyl methacrylate), and so forth, as well as combinations comprising at least one of the foregoing.

Although many of the features of the disposal system 10 are automated, many of the automated features may be manually operable. For example, the door 22 may be manually rotated to either a closed or an open position by hand. Moreover, the tumbler 20 may be counterbalanced to rotate under the weight of the waste placed thereon.

Moreover, the system 10 may not include all of the features illustrated in the exemplary embodiment illustrated in the figures. For example, in another exemplary embodiment not illustrated herein, the door 22 is omitted. In another exemplary embodiment not illustrated herein, the disposal system 10 the tumbler 20 is omitted. In that embodiment, the door 22 limits escapement of the foam. Accordingly, the term moveable component recited in the claims may refer to either the tumbler 20, the door 22, or both.

While preferred embodiments of the invention have been described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A closure for a waste receptacle comprising:
    a first moveable component mounted to said closure for movement relative to the closure between a closed position wherein said first moveable component prohibits waste from entering the waste receptacle, and an open position wherein said first moveable component facilitates the entry of waste into the waste receptacle;
    a second moveable component mounted to said closure for movement relative to the closure between a closed position wherein said second moveable component prohibits waste from entering the waste receptacle, and an open position wherein said second moveable component facilitates the entry of waste into the waste receptacle;
    a motor coupled to both of said first and second moveable components and configured to move said moveable components relative to the closure between said open position and said closed position, the motor having an output shaft, the closure including a rod attached to the output shaft of the motor such that rotational movement of the output shaft causes corresponding rotational movement of the rod; and
    a sensor adapted to transmit a signal when waste is proximal to or contacting said closure, wherein the sensor communicates with the motor to move said first and second moveable components from said open position toward said closed position to deposit the waste into the waste receptacle, wherein the closure defines an aperture through which the waste is inserted.

2. The closure of claim 1, wherein said first moveable component is a door, and said door is configured to expose said aperture to facilitate the entry of waste into the waste receptacle in the open position of said door, and conceal said aperture to prohibit waste from entering the waste receptacle in the closed position of said door.

3. The closure of claim 2, wherein said door is pivotably coupled to said closure to pivot between said open position and said closed position.

4. The closure of claim 1, wherein said second moveable component is a tumbler that is rotatably coupled to said closure, wherein said tumbler is configured to rotate to the open position to facilitate the entry of waste into the waste receptacle.

5. The closure of claim 1, wherein said sensor is a motion sensor adapted to sense waste proximal to said closure.

6. The closure of claim 1, wherein said sensor is a weight sensor adapted to sense waste contactinq said closure.

7. The closure of claim 1, wherein both the first and second moveable components are operatively connected to the rod.

8. The closure of claim 7, further comprising a gear having teeth attached to the rod, and wherein:
    the first moveable component is a door having gear teeth; and
    rotational movement is transferred from the motor to the door through engagement of the teeth of the gear attached to the rod with the gear teeth of the door.

9. The closure of claim 8, wherein:
    the second moveable component is a tumbler having a plurality of arms extending from the rod; and
    at least one of the plurality of arms prohibits waste from entering the waste receptacle when the tumbler is in the closed position.

\* \* \* \* \*